United States Patent [19]

Cleverley et al.

[11] Patent Number: 4,957,642

[45] Date of Patent: Sep. 18, 1990

[54] MAGNESIUM PHENATE DETERGENTS

[75] Inventors: John A. Cleverley, Didcot; John F. Marsh, Abingdon; Philip Skinner, Grove; Gaynor M. Miasik, Cwmdare, all of United Kingdom

[73] Assignee: Exxon Chemical Patents Inc., Linden, N.J.

[21] Appl. No.: 290,024

[22] Filed: Dec. 27, 1988

[30] Foreign Application Priority Data

Dec. 29, 1987 [GB] United Kingdom ................ 8730220

[51] Int. Cl.$^5$ ........................................... C10M 129/10
[52] U.S. Cl. .................................................. 252/42.7
[58] Field of Search ................ 252/33, 37.2, 39, 42.7, 252/18

[56] References Cited

U.S. PATENT DOCUMENTS

| Re. 32,235 | 8/1986 | Forsberg | 252/33 |
|---|---|---|---|
| 3,410,798 | 11/1968 | Cohen | 252/37.2 |
| 3,544,463 | 12/1970 | Koft, Jr. | 252/32.5 |
| 4,049,560 | 9/1977 | Dominey | 252/33.3 |

FOREIGN PATENT DOCUMENTS

| 0095322 | 11/1983 | European Pat. Off. . |
|---|---|---|
| 1189338 | 4/1970 | United Kingdom . |
| 1392255 | 4/1975 | United Kingdom . |

*Primary Examiner*—Jacqueline V. Howard
*Assistant Examiner*—Ellen M. McAvoy
*Attorney, Agent, or Firm*—J. B. Murray, Jr.

[57] ABSTRACT

A magnesium phenate is prepared by a process which comprises reacting (1) magnesium oxide, magnesium hydroxide, magnesium carbonate, magnesium bicarbonate or a magnesium carboxylate with (2) a phenol, a methylene bis-phenol or a sulphurised phenol in the presence of (3) a solvent comprising an organic compound containing one or more alcoholic hydroxyl groups e.g. an alkoxy alcohol and (4) a promoter selected from a ketone, diketone such as $\alpha$ or $\beta$ diketone, aldehyde or carboxylic acid and (5) optionally a diluent oil. This magnesium phenate may be used as a detergent for a lubricating oil.

13 Claims, No Drawings

MAGNESIUM PHENATE DETERGENTS

This invention relates to detergents for lubricating oil compositions.

Various compounds, for example sulphonates and phenates have been used for many years as detergents in lubricating oils and often they contain magnesium or calcium as the cation. Many of these detergents are so called overbased detergents which is a term used to describe compounds containing metal in excess of the amount stoichiometrically required to react with the sulphonic acid or phenol present. Non-overbased detergents are also used alone or in combination with overbased detergents.

U.S. Pat. No. Re 32235 describes a process for making magnesium-containing complexes involving the reaction of magnesium hydroxide, oxide or alkoxide with a carboxylic acid or a sulphonic acid, water and an organic solubilising agent such as certain alcohols or glycols.

G.B. No. 1189338 describes a process for making a basic compound involving the reaction of an alkaline earth metal oxide, an oil soluble organic acid, a neutral or basic sulphonate and a phenol.

G.B. No. 1392255 describes a process for preparing a magnesium/phenate-containing composition involving reacting a certain alkyl phenol with a certain carbonated magnesium alcoholate in the presence of a non-volatile diluent oil and volatile solvent.

Recently there has been a demand for low ash oils and a detergent based on magnesium rather than calcium will have lower ash at equivalent Total Base Number (TBN). Non-overbased magnesium phenates are particularly useful detergents. The preparation of a non-overbased magnesium phenate from magnesium metal via the alkoxide is well known and easily effected. These akloxides must be made from magnesium metal and this is an expensive source of magnesium. Therefore it is desirable to devise a route to a non-overbased megnesium phenate using less expensive sources of magnesiu. However, the preparation of non-overbased magnesium phenate from cheaper sources of magnesium is difficult because of their weak basicity coupled with the weakly acidic nature of an alkyl phenol or a sulphurised alkyl phenol.

EP-A-No. 95322 discloses preparation of alkaline earth metal alkyl phenates by reacting an alkaline earth metal base in a solvent with an inorganic halide as catalyst, and optionally an acid. The use of an inorganic halide as a catalyst makes this route unattractive as environmental considerations make it undesirable to use halogens in processes or to have halogen residues in products for lubricating oil.

We have discovered a method which surprisingly overcomes the difficulties of using cheaper sources of magnesium and is capable of producing very low sediment, easily filterable magnesium phenates or magnesium sulphurised phenates without the use of halogen-containing catalysts.

According to this invention a magnesium phenate is prepared by a process comprising reacting (1) magnesium oxide, magnesium hydroxide, magnesium carbonate, magnesium bicarbonate or a magnesium carboxylate (hereinafter referred to as the magnesium compound) with (2) a phenol, a methylene bis-phenol or a sulphurised phenol in the presence of (3) a solvent comprising an organic compound containing one or more hydroxyl groups and (4) a promoter selected from a ketone, diketone, aldehyde or carboxylic acid and (5) optionally a diluent oil. The process is carried out without the addition of any significant amount of inorganic halide as catalyst.

The magnesium phenates produced by this process can be used as detergents in a lubricating oil. Accordingly, this invention also provides the use as a detergent in a lubricating oil of a magnesium phenate substantially free of inorganic halide prepared by a process comprising reacting (1) magnesium oxide, magnesium hydroxide, magnesium carbonate, magnesium bicarbonate or a magnesium carboxylate (hereinafter referred to as the magnesium compound) with (2) a phenol, a methylene bis-phenol or a sulphurised phenol in the presence of (3) a solvent comprising an organic compound containing one or more alcoholic hydroxyl groups and (4) a promoter selected from a ketone, diketone, aldehyde or carboxylic acid and optionally (5) a diluent oil.

The magnesium compound can include hydrates of the above identified compounds. If a magnesium carboxylate be used the carboxylic acid from which it is derived is preferably a monocarboxylic acid, e.g. one of the formula RCOOH, R being hydrocarbyl, preferably alkyl group of from 1 to 10 carbon atoms. Magnesium acetate and magnesium propionate are suitable examples. The preferred magnesium compound is however magnesium oxide. The type of magnesium oxide used in a preferred embodiment of the process is a light (low bulk density) and active form. Especially suitable are Penine Darlington's Magnesia PDM/02/200 and PDM/02/230 grades. These oxides are desirable since they give a low sediment, fast filtering process with the resultant product having a high TBN.

Although phenol itself could be used as reactant (2) it is preferred that a phenol be used which has attached to the aromatic nucleus one or more groups containing hydrogen and carbon atoms. Such attached groups may be hydrocarbyl, that is containing only hydrogen and carbon atoms, and these are preferably alkyl groups but could also be cycloalkyl, alkenyl, alkynyl, aromatic or a substituted aromatic group such as an alkaryl or aralkyl group. The attached hydrogen - and carbon-containing groups may also contain substituent groups or atoms comprising nitrogen, halogen, oxygen or sulphur atoms. Alternatively, the hydrogen - and carbon-containing group may be bonded to the aromatic ring by a keto or thioketo group. As another alternative the hydrogen - and carbon-containing group may be bonded to the aromatic nucleus by an oxygen, sulphur, or nitrogen atom. Thus, the hydrogen - and carbon-containing group may also be alkoxy, cycloalkoxy, phenoxy, substituted phenoxy, mercaptide, thiophenoxy, substituted thiophenoxy, monoalkyl-amino, dialkylamino, monoarylamino or diaryl-amino.

The total number of carbon atoms per phenol nucleus can vary between 6 and 200 but the preferred number of carbon atoms per phenol nucleus is 10 to 40 per molecule.

The types of phenol from which the reaction product may be derived include:
(i) Substituted phenols of the type

where R is a hydrocarbyl substituent and can be substituted at any position in the phenol ring e.g.: o-cresol, m-cresol, p-cresol, 2-ethylphenol, 3-ethylphenol, 4-ethylphenol, 4-n-butylphenol, 4-sec-butylphenol, 2-t-butylphenol, 4-t-butylphenol, 4-n-pentylphenol, 2-octylphenol, 4-octylphenol, 2-nonylphenol, 4-nonylphenol, 2-dodecylphenol, 4-dodecylphenol, 2-octadecylphenol, 4-octadecylphenol, 2-cyclohexylphenol, 4-allylphenol, 2-phenylphenol, 4-phenylphenol, o-methoxyphenol, p-methoxyphenol and p-phenoxyphenol. Also included are alkyl-phenols where the alkyl group is obtained by polymerisation of a low molecular weight olefin such as ethylene, propylene, n-butylene and isobutylene.

(ii) Di-substituted phenols of the type:

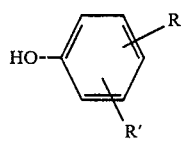

where R and R' are hydrocarbyl substituents and where R and R' may be the same or different, and where R and R' may be substituted at any position in the aromatic ring e.g. 2,3-dimethylphenol, 2,4-dimethylphenol, 2,5-dimethylphenol, 2,6-dimethylphenol; 3,4-dimethylphenol, 2,6-di-n-butylphenol, 2,6-di-sec-butylphenol; 2,6-di-tert-butylphenol; 2,4-di-octylphenol; 2,6-dioctylphenol, 2,4-di-nonylphenol, 2,6-di-nonylphenol; 2,4-di-dodecylphenol; 2,6-di-dodecylphenol; 2,4-di-tert-butylphenol; 2,6-di-allylphenol; 2,4-di-cyclohexylphenol; 2-methyl-5-isopropylphenol and 2-methoxy-4-butylphenol.

(iii) Trisubstituted phenols of the type:

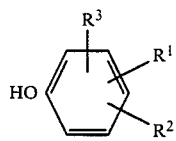

where $R^1$, $R^2$, $R^3$ are hydrocarbyl substituents and where $R^1$, $R^2$, $R^3$ may or may not be the same and where the substitution pattern of the groups is 2,3,4; 2,3,5; 2,3,6; 2,4,5; or 3,4,5; e.g. 2,3,4-trimethylphenol; 2,3,5-trimethylphenol; 2,6-di-t-butyl-3-methylphenol; 2,6-di-t-butyl-3-methoxyphenol etc.

(iv) Tetrasubstituted phenols of the type:

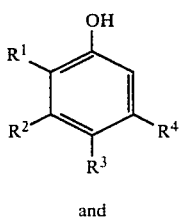

and

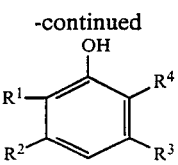

where $R^1$, $R^2$, $R^3$ and $R^4$ are hydrocarbyl substituents and where $R^1$, $R^2$, $R^3$ and $R^4$ may be the same or different, e.g. 2,3,4,5-tetramethylphenol; 4-t-butyl-2,3,5-trimethylphenol; 2,6-di-t-butyl-3,5-dimethylphenol.

(v) Dihydric phenols such as catechol,

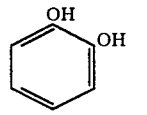

or resorcinol, 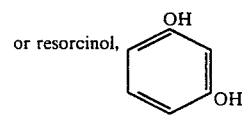

or hydrocarbyl substituted dihydric phenols, e.g. catechol or resorcinol, especially monoalkyl substituted catechol or resorcinol, where examples of hydrocarbyl, e.g. alkyl substituents are as given in (i) above.

(VI) Phenols of the type

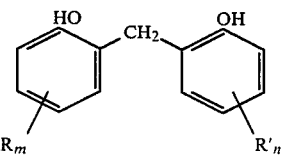

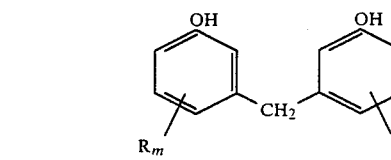

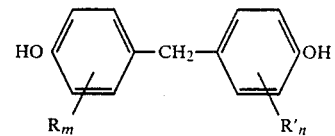

where R and R' are hydrocarbyl substituents which may be different or not and m=n=1 or >1 and/or m>1 with the proviso that at least one of the ortho or para positions on at least one of the phenol aromatic rings remains unsubstituted e.g. 2,2'-dihydroxy-5,5'-dimethyldiphenylmethane; 5,5'-dihydroxy-2,2'-dimethylphenylmethane; 4,4'-dihydroxy-2,2'-dimethyldiphenylmethane; 2,2'-dihydroxy-5,5'-dinonyldiphenylmethane; 2,2'-dihydroxy-5,5'-didodecyldiphenylmethane; 3,3'-di-t-butyl-4,4'-dihydroxydiphenylmethane; 2,2'4,4'-tetra-t-butyl-3,3'-dihydroxydiphenylmethane.

(vi) Sulphurised phenols prepared from the reaction of alkyl phenols, as in (i) to (iv) with, for example, sulphur halides or elemental sulphur.

Examples of such phenols include: 2,2'-thio-bis-(4-methylphenol); 4,4'-di-thio-bis-(2-t-butylphenol); 4,4'thio-bis-(2,6-di-t-butylphenol); 2,2'-di-thio-bis-(4-nonylphenol); 2,2'-thio-bis-(4-nonylphenol); 2,2'-di-thio-bis-(4-dodecylphenol); 2,2'-thio-bis-(4-dodecylphenol); 2,2'-tri-thio-bis-(4-nonylphenol); 2,2'-tetra-thio-bis-(4-nonylphenol); 2 2'-tri-thio-bis-(4-dodecylphenol); 2,2'-tetra-thio-bis-(4-dodecylphenol).

(viii) A mixture of phenols of the types outlined in (i)--(vii).

The mixture of phenols may consist of any number of phenols from any number of the different types outlined above. Alternatively the phenols may be a mixture of phenols of similar structure as for example the mixture of sulphurised phenols that is obtained by reaction of sulphur or sulphur halides with a simple phenol.

The preferred phenol is obtained by the reaction of 4-nonylphenol with sulphur dichloride in any ratio. The most preferred ratio being 2 to 4 parts by weight of 4-nonylphenol to 1 part, by weight, of sulphur dichloride.

The solvent comprises an organic compound containing one or more alcoholic hydroxyl groups. This compound is preferably an aliphatic compound and may be for example an alcohol, a glycol, or an alkoxyalkanol. Suitable compounds preferably contain 1 to 20 carbon atoms, for example 1 to 10 carbon atoms per molecule.

Examples of alcohols include methanol, n-propanol, n-butanol, 4-methyl-pentanol-1, n-decanol, etc. Examples of glycol include ethylene glycol, n-propylene glycol, n-butylene glycol, etc. as well as the oxyalkylene glycols, for example diethylene glycol, triethylene glycol, etc. Trihydric and other polyhydric alcohols could be used, for example glycerol.

The preferred solvent is methanol.

Suitable alkoxyalkanols are the aliphatic alkoxy alkanols, for example the alkoxy ethanols such as methoxyethanol, ethoxyethanol or propoxyethanol. In general suitable alkoxyalkanols will include those of the formula $RO(CH_2)_nOH$ where R is $C_1$ to $C_{10}$ alkyl and n is an integer of from 1 to 10.

The preferred alkoxyalkanol is 2-ethoxyethanol.

The promoter comprises an organic compound selected from a ketone, a diketone such as an $\alpha$ or $\beta$ diketone, an aldehyde or a carboxylic acid and is an important feature of the invention. Without a promoter lower TBNs, higher sediments and slower filtration rates are obtained. Suitable promoters are acetophenone, benzaldehyde and decanoic acid.

Acyl acetones, i.e. compounds of the formula $R^1COCH_2COCH_3$ where $R^1$ is an alkyl group, are very suitable. $R^1$ preferably has 1 to 10 carbon atoms, especially 1 to 5 carbon atoms. Especially preferred as a promoter is acetyl acetone.

A diluent oil is optional and suitable diluent oils for this process will generally be lubricating oils. They can be mineral oils, synthetic oils such as a polyester, a halogenated hydrocarbon or a polyalkylene glycol synthetic lubricating oil.

In order to prepare the magnesium phenate the magnesium compound is mixed with phenol, a methylene bis-phenol or a sulphurized phenol in the presence of the defined solvent and the promoter. It may not be necessary to heat the mixture, but nevertheless, heating is preferred between ambient temperature and the reflux temperature of the mixture.

The relative amounts of magnesium compound and phenol, methylene bis-phenol or sulphurised phenol can vary but in general the weight ratio is determined by the hydroxyl number of the phenol and the magnesium content of the magnesium compound. The preferred ratio is 1 to 12.

The amount of solvent is preferably 0.1 to 10, especially 0.6 to 0.7 times that of the combined weight of the magnesium compound and the phenol, methylene bis-phenol or sulphurised phenol.

The amount of promoter is preferably between 0.001 and 0.1 times, especially 0.01 times that of the combined weight of the magnesium compound and phenol, methylene bis-phenol or sulphurisrd phenol.

It is a surprising feature of the present invention that magnesium phenates may be prepared without the use of inorganic halide catalyst. This simplifies the process and avoids a source of halogen residues in the product. Preferably the reaction mixture contains less than 0.2 wt % inorganic halide, more preferably less than 0.1 wt % inorganic halide, and it is especially preferred that the product is substantially free of halogen - i.e. contains no more than trace amounts (typically no more than 100 ppm) of halogen.

By the process of this invention it is possible to obtain magnesium phenates having a TBN (ASTM D2986) of between 80 and 100, e.g. between 80 to 100 mg KOH/g at 50% active ingredient.

The magnesium phenate may be added, preferably in minor proportion by weight to a lubricating oil to form a lubricating oil composition and particularly preferred proportions are between 0.1 and 20% by weight e.g. between 1.0% and 10% by weight of the total oil composition based on active matter.

Suitable lubricating oils include animal, vegetable or mineral oils, for example petroleum oil fractions ranging from spindle oil to SAE 30, 40 or 50 lubricating oil grades, castor oil, fish oils, oxidised mineral oil or bright-stocks. Synthetic esters, such as diesters or complex esters are suitable.

In addition to the magnesium phenate of this invention the lubricating oil may contain minor amounts by weight of other additives to form lubricating oil compositions (i.e. formulations).

Representative additives typically present in such formulations include viscosity modifiers, corrosion inhibitors, oxidation inhibitors, friction modifiers, dispersants, anti-foaming agents, anti-wear agents, pour point depressants, detergents, rust inhibitors and the like.

Viscosity modifiers impart high and low temperature operability to the lubricating oil and permit it to remain shear stable at elevated temperatures and also exhibit acceptable viscosity or fluidity at low temperatures.

Viscosity modifiers are generally high molecular weight hydrocarbon polymers including polyesters. The viscosity modifiers may also be derivatized to include other properties or functions, such as the addition of dispersancy properties.

These oil soluble viscosity modifying polymers will generally have number average molecular weights of from $10^3$ to $10^6$, preferably $10^4$ to $10^6$, e.g. 20,000 to 250,000, as determined by gel permeation chromatography or membrane osmometry.

Representative examples of suitable viscosity modifiers are any of the types known to the art including polyisobutylene, copolymers of ethylene and propylene, polymethacrylates, methacrylate copolymers, copolymers of an unsaturated dicarboxylic acid and vinyl compound, interpolymers of styrene and acrylic esters, and styrene/isoprene copolymers.

Corrosion inhibitors, also known as anti-corrosive agents, reduce the degradation of the metallic parts contacted by the lubricating oil composition. Illustrative of corrosion inhibitors are phosphosulphurized hydrocarbons and the products obtained by reaction of a phosphosulphurized hydrocarbon with an alkaline earth metal oxide or hydroxide, preferably in the presence of an alkylated phenol or of an alkylphenol thioester, and also preferably in the presence of carbon dioxide. Phosphosulphurized hydrocarbons are prepared by reacting a suitable hydrocarbon such as terpene, a heavy petroleum fraction of a $C_2$ to $C_6$ olefin polymer such as polyisobutylene, with from 5 to 30 wt % of a sulfide of phosphorus for ½ to 15 hours, at a temperature in the range of 150° to 600° F. Neutralization of the phosphosulphurized hydrocarbon may be effected in the manner taught in U.S. Pat. No. 1,969,324.

Oxidation inhibitors reduce the tendency of mineral oils to deteriorate in service which deterioration can be evidenced by the products of oxidation such as sludge and varnish-like deposits on the metal surfaces and by viscosity growth. Such oxidation inhibitors include ZDDP's, aromatic amines such as alkylated diphenylamines and phenyl alpha naphthylamine, hindered phenols, copper compounds, alkaline earth metal salts of alkylphenolthioesters having preferably $C_5$ to $C_{12}$ alkyl side chains, e.g., calcium nonylphenol sulphide, barium t-octylphenyl sulphide, dioctylphenyl-amine, phenylalphanaphthylamine, phosphosulphurized or sulphurized hydrocarbons, etc.

Friction modifiers serve to impact the proper friction characteristics to lubricating oil compositions such as automatic transmission fluids.

Representative examples of suitable friction modifiers are found in U.S. Pat. No. 3,933,659 which discloses fatty acid esters and amides; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses s-carboxyalkylene hydrocarbyl succinimide, s-carboxyalkylene hydrocarbyl succinamic acid and mixtures thereof; U.S. Pat. No. 3,879,306 which discloses N-(hydroxyalkyl)alkenyl-succinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulphurized N-(hydroxyalkyl) alkenyl succinimides. The most preferred friction modifiers are succinate esters, or metal salts thereof, of hydrocarbyl substituted succinic acids or anhydrides and thiobis alkanols such as described in U.S. Pat. No. 4,344,853.

Dispersants maintain oil insolubles, resulting from oxidation during use, in suspension in the fluid thus preventing sludge flocculation and precipitation or deposition on metal parts. Suitable dispersants include high molecular weight alkenyl succinimides, the reaction product of oil-soluble polyisobutylene succinic anhydride with ethylene amines such as tetraethylene pentamine and borated salts thereof.

Pour point depressants lower the temperature at which the fluid will flow or can be poured. Such depressants are well known. Typically of those additives which usefully optimize the low temperature fluidity of the fluid are $C_8$–$C_{18}$ dialkylfumarate vinyl acetate copolymers, polymethacrylates, and wax naphthalene. Foam control can be provided by an antifoamant of the polysiloxane type, e.g., silicone oil and polydimethyl siloxane.

Detergents and metal rust inhibitors include the metal salts of sulphonic acids, alkyl phenols, sulphurized alkyl phenols, alkyl salicylates, naphthenates and other oil soluble mono- and di-carboxylic acids.

Highly basic (viz, overbased) metals salts, such as highly basic alkaline earth metal sulphonates (especially Ca and Mg salts) are frequently used as detergents.

Copper and lead corrosion inhibitors and antiwear agents include borate esters, thiadiazoles such as derivatives of 2,5 dimercapto 1,3,4-thiadiazole and benzotriazoles.

Some of these numerous additives can provide a multiplicity of effects, e.g. a dispersant-oxidation inhibitor. This approach is well known and need not be further elaborated herein.

Compositions when containing these conventional additives are typically blended into the base oil in amounts which are effective to provide their normal attendant function. Representative effective amounts of such additives are illustrated as follows:

| Additive | Vol % | Wt % a.i. |
| --- | --- | --- |
| Vicosity Modifier | .01–4 | .01–4 |
| Corrosion Inhibitor | 0.01–1 | .01–1.5 |
| Oxidation Inhibitor | 0.01–1 | .01–1.5 |
| Dispersant | 0.1–7 | 0.1–8 |
| Pour Point Depressant | 0.01–1 | .01–1.5 |
| Anti-Foaming Agents | 0.001–0.1 | .001–0.15 |
| Anti-Wear Agents | 0.001–1 | .001–1.5 |
| Friction Modifiers | 0.01–1 | .01–1.5 |
| Detergents/Rust Inhibitors | .01–2.5 | .01–3 |
| Mineral Oil Base | Balance | Balance |

When other additives are employed, it may be desirable, although not necessary, to prepare additive concentrates comprising concentrated solutions or dispersions of the dispersant (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the dispersant additive and optional additional additives in proper amounts to provide the desired concentration in the final formulation when the additive-package is combined with a predetermined amount of base lubricant. Thus, the dispersant of the present invention can be added to small amounts of base oil or other compatible solvents along with other desirable additives to form additive-packages containing active ingredients in collective amounts of typically from about 2.5 to about 90%, and preferably from about 5 to about 75%, and most preferably from about 8 to about 50% by weight additives in the appropriate proportions with the remainder being base oil.

The final formulations may employ typically about 10 wt % of the additive-package with the remainder being base oil.

All of said weight percents expressed herein are based on active ingredient (a.i.) content of the additive, and/or upon the total weight of any additive-package, or formulation which will be the sum of the a.i. weight of each additive plus the weight of total oil or diluent.

The magnesium phenate may conveniently be dissolved in a suitable solvent to form a concentrate of from 20 to 90, e.g. 30 to 80 weight percent of the magnesium phenate in the solvent. Suitable solvents include kerosene, aromatic naphthas, mineral lubricating oils etc.

The following Examples illustrate the invention.

EXAMPLE 1

(the preferred route)

Into a one liter, round bottomed, reaction flask, fitted with a stirrer, condenser and gas distribution tube was added 400 g of a 72 mass % solution of nonyl phenol sulphide, 200 g of methanol and 2.9 g acetyl acetone. This mixture was then slowly heated to 50° C. whilst nitrogen was bubbled through it via the gas distribution tube. When the temperature reached 50° C. 22.6 g of magnesium oxide (from Pennine Darlington Magnesia grade 02/200) was added and the temperature raised to 140° C. over 4.5 hours. The temperature was then increased to 160° C. and vacuum was applied. On completion of the vacuum strip, 155 g of Stanco 150 diluent oil was added. After the oil addition a 50 cm$^3$ sample of the product was dissolved in an equal volume of toluene. This toluene solution was then centrifuged to determine the volume of unreacted solids in the product. The level of unreacted solids was obtained by multiplying the observed sediment in the toluene solution by two. This is then reported as the pre-filtration sediment. In the above experiment a pre-filtration sediment of 0.1 volume % was found. The product was then filtered through a bed of diatomaceous earth in a pressure filter where a rate of 497 litres/m$^2$/hr was obtained. The finished product had a TBN of 85 mg KOH/g, a viscosity of 48 cST at 100° C. and contained 1.86% Mg and 5.0% sulphur.

EXAMPLE 2

Example 2 illustrated the use of 2-ethoxyethanol as a replacement solvent for methanol.

The conditions and amounts were the same as for Example 1 except 200 g of 2-ethoxyethanol was used in place of the methanol. The resultant product had a pre-filtration sediment of 0.06 vol %, filtered at a rate of 1616 liters/meters$^2$/hr, a TBN of 93 mg KOH/g and contained 2.06 mass % magnesium.

EXAMPLE 3

(comparative)

Example 3 demonstrates the need for a promoter. Example 1 was repeated except the acetyl acetone was omitted. The product had a pre-filtration sediment of 2.5 vol %, filtered at 91 l/m$^2$/hr, a TBN of 76 mg KOH/g and contained 1.73% magnesium.

EXAMPLE 4

(comparative)

Example 4 also demonstrates the need for a promoter. Example 2 was repeated except the acetyl acetone was omitted. The unfiltered product had a sediment of 0.05 vol %. After a slow filtration of 207 l/m$^2$/hr the finished product had a TBN of 72 mg KOH/g and contained 1.66% Mg.

EXAMPLE 5

This illustrates the use of acetophenone as a promoter. Example 2 was repeated except acetophenone was used in place of the acetyl acetone and Magchem 50 magnesium oxide was used. The product had a pre-filtration sediment of 1.8 vol %, filtered at 374 l/m$^2$/hr and had a TBN of 78 mg KOH/g.

EXAMPLE 6

This illustrates the use of decanoic acid as promoter. Example 1 was repeated except the acetyl acetone was replaced by decanoic acid. The product although filtering slowly had a TBN of 80 mg KOH/g.

We claim:

1. A process for preparing a non-overbased magnesium phenate which comprises reacting a reaction mixture consisting essentially of (1) a magnesium compound (2) a phenol, a methylene bis-phenol or a sulphurised phenol, (3) an organic solvent containing one or more alcoholic hydroxyl groups, (4) a promoter selected from a ketone, diketone, and aldehyde and (5) optionally a diluent oil, said reaction mixture containing less than 0.2 wt. % of inorganic halide.

2. A process according to claim 1 wherein the magnesium compound is magnesium oxide.

3. A process according to claim 1 wherein the sulphurised phenol is the reaction product obtained by the reaction of 4-nonyl phenol with sulphur dichloride.

4. A process according to claim 1 wherein the solvent is methanol.

5. A process according to claim 1 wherein the solvent is an alkoxyalkanol of the formula $RO(CH_2)_nOH$ where R is $C_1$ to $C_{10}$ alkyl and n is an integer of from 1 to 10.

6. A process according to claim 5 wherein the alkoxyalkanol is 2-ethoxyethanol.

7. A process according to claim 1 wherein the promoter is an acyl acetone of the formula $R^1COCH_2COCH_3$ where $R^1$ is an alkyl group.

8. A process according to claim 7 wherein the group $R^1$ in the acyl acetone has 1 to 5 carbon atoms.

9. A process according to claim 8 wherein the acylacetone is acetyl acetone.

10. A process according to claim 1 wherein the reaction takes place in the presence of a diluent oil.

11. A magnesium phenate prepared by the process according to claim 1.

12. A lubricating oil composition comprising a lubricating oil and the magnesium phenate prepared by the process according to claim 1.

13. A concentrate comprising a solvent and 20 to 90 weight percent of the magnesium phenate prepared by the process according to claim 1.

* * * * *